United States Patent [19]

Soula

[11] 4,417,081
[45] Nov. 22, 1983

[54] SELECTIVE 2-CHLORINATION OF META-DIHALOBENZENES

[75] Inventor: Gerard Soula, Meyzieu, France

[73] Assignee: Rhone-Poulenc Specialites Chimiques, Courbevoie, France

[21] Appl. No.: 428,451

[22] Filed: Sep. 30, 1982

[30] Foreign Application Priority Data

Oct. 2, 1981 [FR] France .............................. 81 18585

[51] Int. Cl.$^3$ ............................................ C07C 17/12
[52] U.S. Cl. .................................... 570/147; 570/208; 570/209
[58] Field of Search ............... 570/147, 208, 207, 206, 570/209

[56] References Cited

U.S. PATENT DOCUMENTS 2,843,637  7/1958  Clarke et al. ...................... 570/207

Primary Examiner—Charles F. Warren
Assistant Examiner—Joseph A. Boska
Attorney, Agent, or Firm—Burns, Doane, Swecker & Mathis

[57] ABSTRACT

The meta-dihalobenzenes are selectively 2-chlorinated by reacting same with a chlorine donor, e.g., hexachlorobenzene or pentachlorobenzene, in the presence of at least one alkali metal amide, e.g., sodamide, and at least one compound which complexes the cation of such at least one alkali metal amide.

21 Claims, No Drawings

SELECTIVE 2-CHLORINATION OF META-DIHALOBENZENES

BACKGROUND OF THE INVENTION

1. Field of the Invention

The present invention relates to the selective chlorination of meta-dihalobenzenes, and, more especially, to such chlorination by reacting a meta-dihalobenzene with a chlorine donor, in the presence of at least one alkali metal amide and at least one compound adapted to complex the cation of said alkali metal amide.

2. Description of the Prior Art

Various processes for the chlorination of halogenated compounds employing an acid catalyst are of course well known to this art.

Thus, the chlorination of such halo-compounds by means of gaseous chlorine in the presence of ferric chloride or aluminum chloride is representative. Compare, in particular, C. A. Thomas, *Anhydrous Aluminum Chloride in Organic Chemistry* (Reinhold Publishing Corporation).

The presence of a halogen atom on the aromatic nucleus orients, under the aforenoted conditions, the chlorination to ortho-, para-. Experimentally, preferential chlorination in the para-position is observed.

As regards the meta-dihalocompounds, the chlorination thereof is essentially of the 4-position. For example, chlorination of meta-dichlorobenzene principally yields 1,2,4-trichlorobenzene.

Selective chlorination of the 2-position cannot be carried out in this manner. Such compounds have been obtained in the prior art only by indirect means.

SUMMARY OF THE INVENTION

Accordingly, a major object of the present invention is the provision of an improved process for the selective 2-position chlorination of the meta-dihalobenzenes, and which improved process is predicated upon a marked departure from the conventional chlorination reactions, in that the reaction is carried out in the presence of basic catalysts vis-a-vis the acid catalysts which characterize the prior art.

Briefly, the present invention features the chlorination of meta-dihalobenzenes, by reacting a meta-dihalobenzene with a chlorine-donating compound ("chlorine donor") in the presence of at least one alkali metal amide and at least one compound which complexes the cation of such at least one amide.

DETAILED DESCRIPTION OF THE INVENTION

More particularly according to this invention, in a first embodiment thereof, the compound which complexes the cation of the at least one amide is a sequestering agent having the structural formula (I):

$$N + CHR_1 - CHR_2 - O - (CHR_3 - CHR_4 - O) - {}_n - R_5]_3 \quad (I)$$

wherein n is an integer greater than or equal to 0 and less than or equal to approximately 10 ($0 \leq n \leq 10$), $R_1$, $R_2$, $R_3$, $R_4$, which may be identical or different, each represents a hydrogen atom or an alkyl radical having from 1 to 4 carbon atoms and $R_5$ represents an alkyl or cycloalkyl radical having from 1 to 12 carbon atoms, a phenyl radical or a radical with the formula $-C_mH_{2m}-\phi$, or $C_mH_{2m+1}-\phi-$, with m ranging from 1 to about 12 and $\phi$ being phenyl.

In a second embodiment of the invention, the compound which complexes the cation of the at least one amide is a macrocyclic polyether having from 15 to 30 atoms in the ring and comprising from 4 to 10 —O—X units, wherein X is either —CHR$_6$—CHR$_7$— or —CHR$_6$—CHR$_8$—CR$_9$R$_7$—, with R$_6$, R$_7$, R$_8$ and R$_9$, which also may be identical or different, each being a hydrogen atom or an alkyl radical having from 1 to 4 carbon atoms, with one X moiety optionally being —CHR$_6$—CHR$_8$—CR$_9$R$_7$— when the —O—X units comprise the group —O—CHR$_6$—CHR$_7$—.

And in a third embodiment of the invention, the compound which complexes the cation of the at least one amide is a macrocyclic or bicyclic compound having one of the structural formulae (IIa) or (IIb):

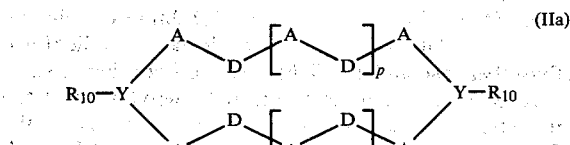
(IIa)

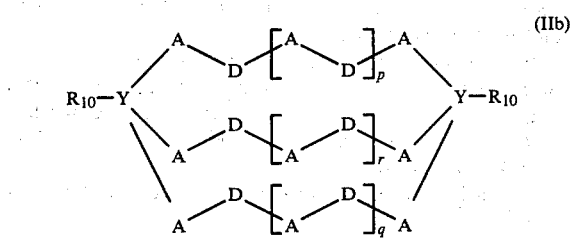
(IIb)

wherein Y represents N or P; A represents an alkylene radical having from 1 to 3 carbon atoms; D represents O, S or N—R$_{11}$, with R$_{11}$ being an alkyl radical having from 1 to 6 carbon atoms; R$_{10}$ represents an alkyl radical having from 1 to 6 carbon atoms; and p, q and r, which may be identical or different, are each integers ranging from 1 to 5.

The invention also envisages the use of at least two of the aforedescribed complexing compounds.

The alkali metal amide employed within the scope of the present invention is preferably selected from among sodium amide, potassium amide and lithium amide.

Sodium amide is particularly preferred.

The chlorine donor is preferably selected from among hexachlorobenzene and pentachlorobenzene.

The meta-dihalobenzene starting materials according to the present invention preferably have the following structural formula (III):

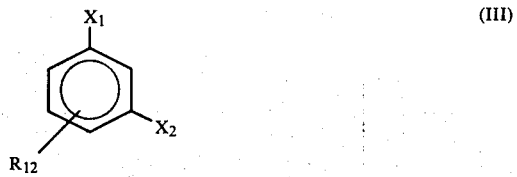
(III)

wherein $X_1$ and $X_2$, which may be identical or different, each represents Cl or F, and $R_{12}$, which cannot be in the 2-position, represents Cl, F or an alkyl radical having from 1 to 6 carbon atoms.

Exemplary of such meta-dihalobenzene starting materials, the following compounds are representative:

meta-dichlorobenzene, 2,4-dichlorotoluene, meta-fluorochlorobenzene, meta-difluorobenzene, chloro-2,4-difluorobenzene and 2,4-difluorotoluene.

The final products obtained according to this invention have the following structural formula (IV):

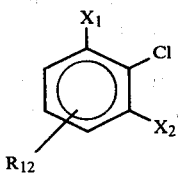

(IV)

wherein $X_1$, $X_2$ and $R_{12}$ are as above-defined.

The product compounds are useful intermediates in a variety of organic syntheses.

The invention is of particular interest for the preparation of the following compounds: 1,3-difluoro-2-chlorobenzene, 2,4-difluoro-3-chlorotoluene, 2,3-dichlorofluorobenzene and 1,3-dichloro-2,4-difluorobenzene.

According to another preferred embodiment of the invention, at least one sequestering agent having the formula (I) is used, in which $R_1$, $R_2$, $R_3$ and $R_4$ each represent a hydrogen atom or a methyl radical, and $R_5$ and n are as above-defined.

Among such preferred sequestering agents, it is even more particularly preferred to employ those in which n is greater than or equal to 0 and less than or equal to 6 and wherein $R_5$ represents an alkyl radical having from 1 to 4 carbon atoms.

The following sequestering agents are noted as illustrative:

[1] tris-(3-oxabutyl)-amine of the formula:

N—(CH$_2$—CH$_2$—O—CH$_3$)$_3$,

[2] tris-(3,6-dioxaheptyl)-amine of the formula:

N—(CH$_2$—CH$_2$—O—CH$_2$—CH$_2$—O—CH$_3$)$_3$,

[3] tris-(3,6,9-trioxadecyl)-amine of the formula:

N—(CH$_2$—CH$_2$—O—CH$_2$—CH$_2$—O—CH$_2$—CH$_2$—O—CH$_3$)$_3$,

[4] tris-(3,6-dioxaoctyl)-amine of the formula:

N—(CH$_2$—CH$_2$—O—CH$_2$—CH$_2$—O—C$_2$H$_5$)$_3$,

[5] tris-(3,6,9-trioxaundecyl)-amine of the formula:

N—(CH$_2$—CH$_2$—O—CH$_2$—CH$_2$—O—CH$_2$—CH$_2$—O—C$_2$H$_5$)$_3$,

[6] tris-(3,6-dioxanonyl)-amine of the formula:

N—(CH$_2$—CH$_2$—O—CH$_2$—CH$_2$—O—C$_3$H$_7$)$_3$,

[7] tris-(3,6,9-trioxadodecyl)-amine of the formula:

N—(CH$_2$—CH$_2$—O—CH$_2$—CH$_2$—O—CH$_2$—CH$_2$—O—C$_3$H$_7$)$_3$,

[8] tris-(3,6-dioxadecyl)-amine of the formula:

N—(CH$_2$—CH$_2$—O—CH$_2$—CH$_2$—O—C$_4$H$_9$)$_3$,

[9] tris-(3,6,9-trioxatridecyl)-amine of the formula:

N—(CH$_2$—CH$_2$—O—CH$_2$—CH$_2$—O—CH$_2$—CH$_2$—O—C$_4$H$_9$)$_3$,

[10] tris-(3,6,9,12-tetraoxatridecyl)-amine of the formula:

N—[(CH$_2$—CH$_2$—O—)$_3$—CH$_3$]$_3$,

[11] tris-(3,6,9,12,15,18-hexaoxanonadecyl)-amine of the formula:

N—[(CH$_2$—CH$_2$—O—)$_5$CH$_3$]$_3$,

[12] tris-(3,6-dioxa-4-methylheptyl)-amine of the formula:

N—(CH$_2$—CH$_2$—O—CH(CH$_3$)—CH$_2$—O—CH$_3$)$_3$, and

[13] tris-(3,6-dioxa-2,4-dimethylheptyl)-amine of the formula:

N—(CH$_2$—CH(CH$_3$)—O—CH(CH$_3$)—CH$_2$—O—CH$_3$)$_3$.

The preparation of the aforesaid sequestering agents is described in French Application No. 79/05438, published under No. 2,450,120.

The macrocyclic polyethers which also may be employed in the process according to the invention are generically known to the art as "crown ethers" and are described, for example, in French Application No. 69/43879, published under No. 2,026,481.

Exemplary of the crown ethers that may be used according to the invention, the following are representative:

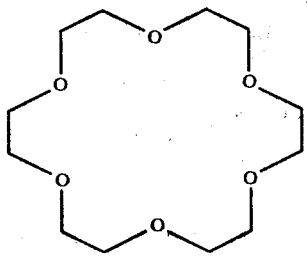

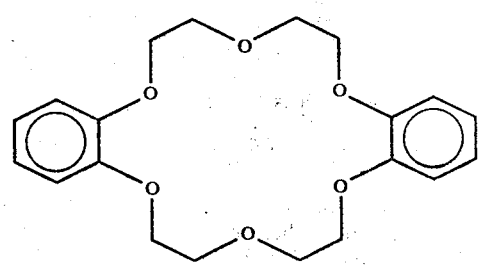

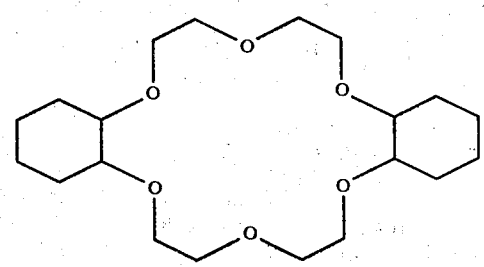

-continued

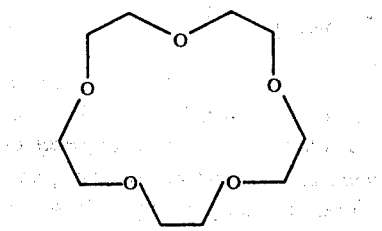

The macrocyclic and bicyclic compounds which can be used are described in French Application No. 70/21079, published under No. 2,052,947. The following are representative of such compounds suitable for use in the process according to the invention:

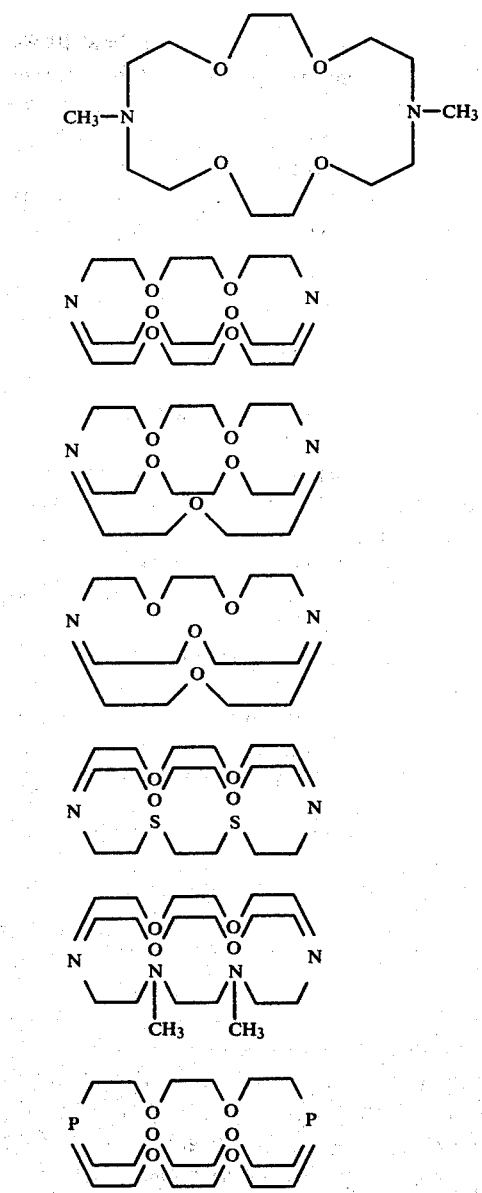

The process according to the invention may be carried out in the presence of a third component solvent, or in the absence of such solvent. When a solvent is indeed employed, it is preferably selected from among the aprotic apolar solvents, or the slightly polar, aprotic solvents, such as, for example, benzene, toluene, chlorobenzene, and the like.

The process, though, can also be carried out in the absence of solvent; in this case, the chlorinating agent itself plays the role of the solvent.

In accordance herewith, it is theorized that the product of the reaction between the alkali metal amide and the meta-dihalobenzene, which may be represented by the structural formula below, in the case wherein the alkali metal amide is sodium amide, is solubilized entirely or partially in the reaction medium by the complexing of the amide cation with the agent of complexation:

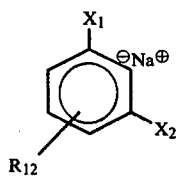

Such solubilization enables reaction with the chlorine donor, with the latter being converted into its lower analog (for example, into pentachlorobenzene, when hexachlorobenzene is used).

According to the process of the invention, an amount of the alkali metal amide is used such that the molar ratio of the alkali metal amide to the compound having the structural formula (III) preferably ranges from about 0.05 to about 1. Even more preferably, such ratio ranges from about 0.1 to about 0.5.

The chlorine donor is employed in amounts such that the molar ratio of donor compound to the compound having the formula (III) preferably ranges from about 0.3 to about 1.

Even more preferably, such ratio ranges from about 0.7 to about 1.

The complexing compound is used in amounts such that the molar ratio of the complexing agent to the compound having the formula (III) preferably ranges from about 0.01 to about 0.2. Even more preferably, such ratio ranges from about 0.03 to about 0.1.

The reaction is typically carried out at a temperature ranging from about $-30°$ C. to about $50°$ C.

Preferably, the reaction is carried out at ambient temperature under atmospheric pressure.

In order to further illustrate the present invention and advantages thereof, the following specific examples are given, it being understood that same are intended only as illustrative and in nowise limitative.

EXAMPLE 1

Chlorination of 1,3-dichlorobenzene with hexachlorobenzene

Into a 10 cm$^3$ reactor, equipped with magnetic agitation, 1.5 g (0.01 mole) 1,3-dichlorobenzene dissolved in 1.5 g chlorobenzene and 1.42 g (0.005 mole) hexachlorobenzene were successively charged.

Subsequently, 0.16 g tris(3,6-dioxaheptyl)amine, or 5% in moles with respect to the 1,3-dichlorobenzene, was added thereto.

The temperature of the reaction mixture was maintained under agitation at 20° C., while 0.15 g sodium amide (NaNH$_2$) was added thereto as a 50% solution in toluene (0.002 mole).

After a contact time of one hour, the crude reaction mixture was analyzed by vapor phase chromatography.

The composition of the reaction mixture was as follows: 1,2,3-trichlorobenzene (90%); 1,2,4-trichlorobenzene (5%); 1,3,5-trichlorobenzene (5%). The degree of conversion was 62% and the yield was 88%.

EXAMPLE 2

Chlorination of 1,3-difluorobenzene with hexachlorobenzene

Into a 5 cm³ reactor equipped with magnetic agitation, 0.57 g (0.005 mole) 1,3-difluorobenzene dissolved in 0.57 g chlorobenzene and 0.71 g (0.0025 mole) hexachlorobenzene were successively charged.

Subsequently, 0.08 g of tris(3,6-dioxaheptyl)amine, or 5% in moles with respect to the 1,3-difluorobenzene, was added thereto.

The temperature of the reaction mixture was maintained under agitation at 20° C. Next, 0.075 g sodium amide (NaNH$_2$) as a 50% solution in toluene (0.001 mole) was added thereto.

After a contact time of 30 minutes, the crude reaction mixture was analyzed by vapor phase chromatography.

The degree of conversion was approximately 50% and the yield in 2,6-difluorochlorobenzene was 87%.

EXAMPLE 3

Chlorination of 1-fluoro-3-chlorobenzene with hexachlorobenzene

Into a 10 cm³ reactor equipped with magnetic agitation, 1.3 g (0.01 mole) 1-fluoro-3-chlorobenzene, dissolved in 1.3 g chlorobenzene, and 1.42 g (0.005 mole) hexachlorobenzene, were successively charged.

Subsequently, 0.16 g tris(3,6-dioxaheptyl)amine, or 5% in moles with respect to the 1-fluoro-3-chlorobenzene, was added thereto.

The temperature of the reaction mixture was maintained under agitation at 20° C. 0.14 g sodium amide (NaNH$_2$) was then added thereto as a 50% solution in toluene (0.0018 mole).

After a contact time of 20 minutes, the crude reaction mixture was analyzed by vapor phase chromatography.

2,3-Dichlorofluorobenzene was formed in a yield of 65%.

EXAMPLE 4

Chlorination of 2,4-difluorochlorobenzene with hexachlorobenzene

Into a 150 cm³ reactor, equipped with magnetic agitation, 22.2 g (0.15 mole) 2,4-difluorochlorobenzene dissolved in 22.2 toluene, and 28.5 g (0.1 mole) hexachlorobenzene (28.5 g), were successively charged.

4.85 g tris(3,6-dioxaheptyl)amine, or 5% in moles with respect to the 2,4-difluorochlorobenzene, were next added thereto.

The temperature of the reaction mixture was maintained under agitation at 20° C.; 5.8 g sodium amide (NaNH$_2$) as a 50% solution in toluene (0.075 mole) were then added thereto.

After a contact time of 20 minutes, the crude reaction mixture was analyzed by vapor phase chromatography.

2,4-Difluoro-1,3-dichlorobenzene was obtained in a yield of 61%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the selective 2-chlorination of a meta-dihalobenzene, comprising reacting such meta-dihalobenzene with a chlorine donor in the presence of at least one alkali metal amide and at least one compound which complexes the cation of such at least one alkali metal amide.

2. The process as defined in claim 1, said complexing compound comprising a tertiary amine sequestering agent having the structural formula (I):

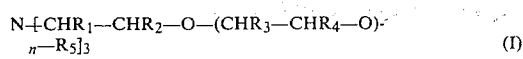

$$N\text{-}[CHR_1\text{---}CHR_2\text{---}O\text{---}(CHR_3\text{---}CHR_4\text{---}O)_n\text{---}R_5]_3 \quad (I)$$

wherein n is an integer ranging from 0 to about 10, R$_1$, R$_2$, R$_3$, R$_4$, which may be identical or different, each represents a hydrogen atom or an alkyl radical having from 1 to 4 carbon atoms and R$_5$ represents an alkyl or cycloalkyl radical having from 1 to 12 carbon atoms, a phenyl radical or a radical having the formula —C$_m$H$_{2m}$—φ, or C$_m$H$_{2m+1}$—φ—, with m ranging from 1 to about 12 and φ being phenyl.

3. The process as defined by claim 2, wherein the sequestering agent having the formula (I), R$_1$, R$_2$, R$_3$ and R$_4$ are each hydrogen or methyl.

4. The process as defined by claims 2 or 3, wherein the sequestering agent having the formula (I), n is an integer ranging from 0 to 6.

5. The process as defined by claims 2 or 3, wherein the sequestering agent having the formula (I), R$_5$ is an alkyl radical having from 1 to 4 carbon atoms.

6. The process as defined by claim 2, said sequestering agent having the formula (I) comprising tris(3,6-dioxaheptyl)amine.

7. The process as defined by claim 2, said sequestering agent having the formula (I) comprising tris(3-oxabutyl)amine, tris(3,6-dioxaheptyl)amine, tris(3,6,9-trioxadecyl)amine, tris(3,6-dioxaoctyl)amine, tris(3,6,9-trioxaundecyl)amine, tris(3,6-dioxanonyl)amine, tris(3,6,9-trioxadodecyl)amine, tris(3,6-dioxadecyl)amine, tris(3,6,9-trioxatridecyl)amine, tris(3,6,9,12-tetraoxatridecyl)amine, tris(3,6,9,12,15,18-hexaoxanonadecyl)amine, tris(3,6-dioxa-4-methylheptyl)amine or tris(3,6-dioxa-2,4-dimethylheptyl)amine.

8. The process as defined by claim 1, said complexing compound comprising a macrocyclic polyether having from 15 to 30 atoms in the ring and comprising from 4 to 10 —O—X units, wherein X is either —CHR$_6$—CHR$_7$— or —CHR$_6$—CHR$_8$—CR$_9$R$_7$—, with R$_6$, R$_7$, R$_8$ and R$_9$, which may be identical or different, each being a hydrogen atom or an alkyl radical having from 1 to 4 carbon atoms, and further wherein one X moiety may be —CHR$_6$—CHR$_8$—CR$_9$R$_7$— when the —O—X units comprise the group —O—CHR$_6$—CHR$_7$—.

9. The process as defined by claim 8, said macrocyclic polyether comprising:

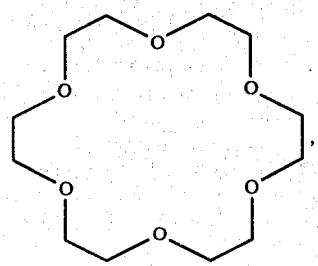

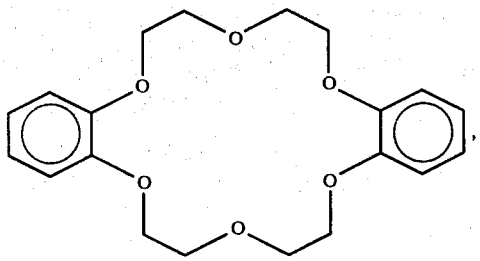,

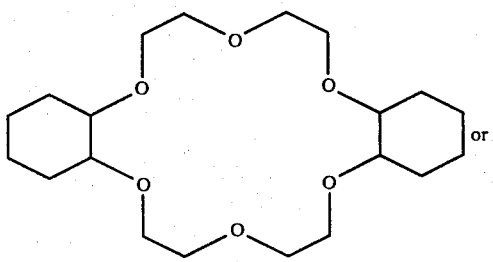 or

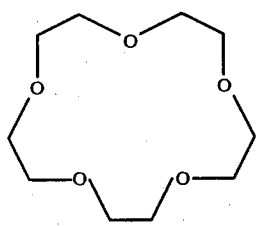

10. The process as defined by claim 1, said complexing compound comprising a macrocyclic or bicyclic compound having one of the structural formulae (IIa) or (IIb):

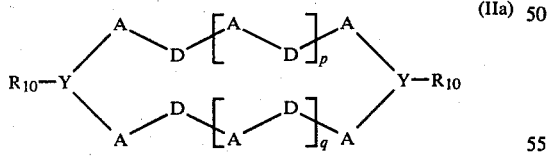 (IIa)

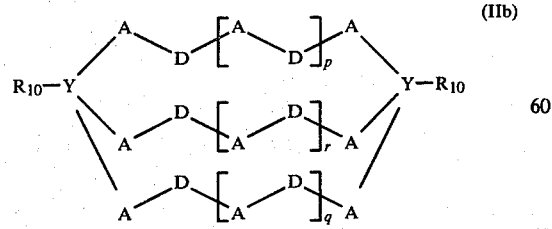 (IIb)

wherein Y represents N or P; A represents an alkylene radical having from 1 to 3 carbon atoms; D represents O, S or N—$R_{11}$, with $R_{11}$ being an alkyl radical having from 1 to 6 carbon atoms; $R_{10}$ represents an alkyl radical having from 1 to 6 carbon atoms; and p, q and r, which may be identical or different, are each integers ranging from 1 to 5.

11. The process as defined by claim 10, said macrocyclic or bicyclic compound comprising:

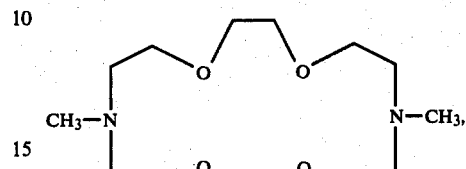

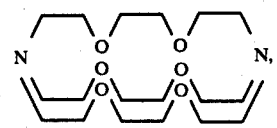

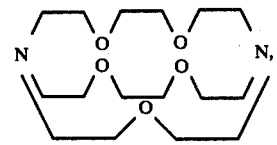

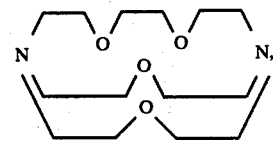

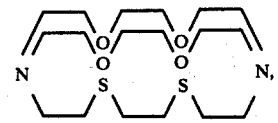

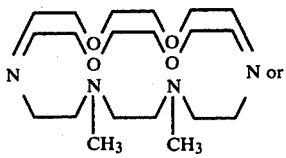 N or

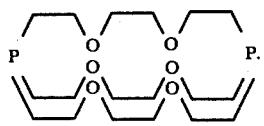

12. The process as defined by any of claims 1, 2, 8 or 10, said at least one alkali metal amide comprising sodium, potassium or lithium amide.

13. The process as defined by claim 12, said at least one alkali metal amide comprising sodamide.

14. The process as defined by any of claims 1, 2, 8 or 10, said starting material meta-dihalobenzene having the structural formula (III):

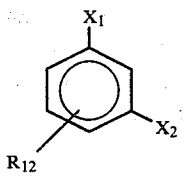
(III)

wherein $X_1$ and $X_2$, which may be the same or different, are each chloro or fluoro, and $R_{12}$, which cannot be in the 2-position, is chloro, fluoro or an alkyl radical having from 1 to 6 carbon atoms.

15. The process as defined by any of claims 1, 2, 8 or 10, said chlorine donor comprising hexachlorobenzene or pentachlorobenzene.

16. The process as defined by claim 1, said reaction being carried out in the presence of an aprotic apolar or slightly polar solvent.

17. The process as defined by claim 16, said solvent comprising benzene, toluene or chlorobenzene.

18. The process as defined by claim 1, wherein the molar ratio of the at least one alkali metal amide to the starting material meta-dihalobenzene ranges from about 0.05 to about 1.

19. The process as defined by claim 18, wherein the molar ratio of the chlorine donor to the starting material meta-dihalobenzene ranges from about 0.3 to about 1.

20. The process as defined by claim 19, wherein the molar ratio of the complexing compound to the starting material meta-dihalobenzene ranges from about 0.01 to about 0.2.

21. The process as defined by claim 20, said reaction being carried out at a temperature ranging from about −30° C. to about 50° C.

* * * * *